United States Patent [19]

McCall

[11] Patent Number: 4,743,444

[45] Date of Patent: May 10, 1988

[54] ANTIPERSPIRANT AND DEODORANT STICKS

[75] Inventor: Patrick C. McCall, Cincinnati, Ohio

[73] Assignee: The Procter & Gamble Company, Cincinnati, Ohio

[21] Appl. No.: 832,092

[22] Filed: Feb. 20, 1986

[51] Int. Cl.$^4$ .......................... A61K 7/32; A61K 7/34; A61K 7/36; A61K 7/38

[52] U.S. Cl. ................ 424/65; 424/DIG. 5; 424/66; 424/67; 424/68

[58] Field of Search ............... 424/65, 66, 67, 68, 424/DIG. 5

[56] References Cited

U.S. PATENT DOCUMENTS

| | | | |
|---|---|---|---|
| 4,126,679 | 11/1978 | Davy et al. | 424/66 |
| 4,154,816 | 5/1979 | Roehl et al. | 424/68 |
| 4,346,079 | 8/1982 | Roehl | 424/65 |
| 4,414,200 | 11/1983 | Murphy et al. | 424/66 |
| 4,425,328 | 1/1984 | Nabial | 424/DIG. 5 |
| 4,511,554 | 4/1985 | Geria et al. | 424/66 |
| 4,518,582 | 5/1985 | Schamper et al. | 424/DIG. 5 |

FOREIGN PATENT DOCUMENTS

| | | | |
|---|---|---|---|
| 120210 | 10/1984 | European Pat. Off. | 424/66 |
| 1291819 | 10/1972 | United Kingdom | 544/474 |
| 2139496 | 5/1983 | United Kingdom | 424/66 |

OTHER PUBLICATIONS

Scott et al., J. Soc. Cosmet. Chem., 5/1979, vol. 30, pp. 137–156.
Drug & Cosmetic Industry, 11/1978, pp. 122.
Chem. Abs., 1976, vol. 85, 10309b, Kunimura et al.

*Primary Examiner*—Dale R. Ore
*Attorney, Agent, or Firm*—David K. Dabbiere; David L. Suter; Douglas C. Mohl

[57] ABSTRACT

Cosmetic stick compositions comprising from about 10% to about 97% of a liquid base material, from about 1% to about 10% of a benzylidene sorbitol, and from about 1% to about 15% of a $C_{14}$–$C_{16}$ fatty alcohol. Cetyl alcohol is a preferred $C_{14}$–$C_{16}$ fatty alcohol. The cosmetic sticks preferably also contain an active material, such as an antiperspirant active or a deodorant active.

9 Claims, No Drawings

ANTIPERSPIRANT AND DEODORANT STICKS

BACKGROUND OF THE INVENTION

The present invention relates to stick-type cosmetic compositions. More particularly, it relates to improved deodorant sticks.

The chemical and cosmetic literature is replete with formulations of stick-form cosmetics for various uses, such as antiperspirants, deodorants, and lipsticks. The specific stick formulation may vary depending upon such factors as the intended use, the "active" ingredient to be incorporated, and the part of the body to which the product is to be applied.

There are three main types of such cosmetic stick formulations: compressed power sticks, gel sticks, and wax sticks. While each of these formulation types may have advantages in certain use situations, each also has disadvantages. For example, compressed powder sticks are often brittle and hard, and leave a cosmetically-unacceptable dust upon application. Gels, while offering very good aesthetic characteristics, may be unstable due to interaction of the soap gelling agents typically used to solidify such sticks with the stick's "active" material (e.g., the astringent metallic salts used in antiperspirant sticks). Wax-based formulations can also yield cosmetically-unacceptable products due to such factors such as hardness, greasiness, and stickiness. The opacity of such wax sticks, and the residue created in their use, may also be aesthetically undesirable.

Many stick formulations have been described in the literature which attempt to maintain the desirable cosmetic and aesthetic attributes of gel sticks, while minimizing the disadvantages of gel sticks. For example, antiperspirant gel sticks, using dibenzaldehyde monosorbitol acetal (herein "DBMSA") as a gelling agent, are described in U.S. Pat. No. 4,154,816, Roehl, et al., issued May 15, 1979, U.S. Pat. No. 4,346,079, Roehl, issued Aug. 24, 1982, and U.S. Pat. No. 4,518,582, Schamper, et al., issued May 21, 1985. Deodorant sticks using DBMSA are described in Japanese Pat. No. 50/52,007, published Apr. 9, 1975. Nevertheless, it has been found that such DBMSA sticks, while avoiding the use of soaps, may produce sticks of aesthetically unacceptable softness. While hardness of such sticks may be increased by use of increased levels of DBMSA, such levels may require excessive heating of product materials during manufacturing so as to fully solubilize the DBMSA. The use of such high levels, with heating, presents disadvantages due to cost, safety, and thermal degradation of some materials, such as "active" materials or fragrances. Hardness can also be increased using other gelling agents (such as sodium stearate) with DBMSA, but also incurring the disadvantages associated with such other agents, as described above.

It has now been discovered that solid cosmetic sticks using DBMSA as a gelling agent, and also containing certain fatty alcohols, are cosmetically and aesthetically acceptable sticks. In particular, such sticks of this invention afford gel rheologic characteristics and gel transparency, while maintaining hardness and physical integrity more typical of wax-based cosmetic sticks. Such benefits can be obtained without using disadvantageous levels of DBMSA and/or other gelling agents.

SUMMARY OF THE INVENTION

The present invention provides solid cosmetic stick compositions comprising:
(a) from about 10% to about 97% of a liquid base material;
(b) from about 1% to about 10% of a benzylidene sorbitol; and
(c) from about 1% to about 15% of a $C_{14}$–$C_{16}$ fatty alcohol.

This invention also provides cosmetic sticks, further comprising from about 10% to about 50% of one or more astringent metallic salts, particularly useful as antiperspirants. Also provided are deodorant cosmetic sticks, additionally containing a safe and effective amount of a deodorant active material.

DESCRIPTION OF THE INVENTION

The cosmetic sticks of this invention contain three essential ingredients: liquid base materials, a benzylidene sorbitol, and a $C_{14}$–$C_{16}$ fatty alcohol. These compositions (herein "cosmetic sticks") encompass any solid (or semi-solid) composition intended for human use in order to deposit material on human skin. Thus, these cosmetic sticks preferably contain additional ingredients, depending upon their intended use, such as antiperspirant salts and deodorizing compounds. These essential and optional ingredients must be "cosmetically-acceptable", i.e., safe for human use and aesthetically acceptable at the levels at which such materials are used in the present compositions, at a reasonable risk/benefit ratio.

Specifically, the cosmetic sticks of the present invention comprise:
(a) from about 10% to about 97% of a liquid base material;
(b) from about 1% to about 10% of a benzylidene sorbitol; and
(c) from about 1% to about 15% of a $C_{14}$–$C_{16}$ fatty alcohol.

(As used herein, all percentages are by weight of total composition.) The liquid base materials are preferably present at levels of from about 30% to about 95%, more preferably from about 60% to about 95%. The benzylidene sorbitol is preferably present at a level of from about 1.5% to about 5%, more preferably from about 2.5% to about 3.5%. The $C_{14}$–$C_{16}$ fatty alcohol is preferably present at a level of from about 1% to about 10%, more preferably from about 3% to about 7%.

The specific essential and non-essential materials to be included, and their levels, are selected in order to produce a stick of desired hardness, so as to maintain dimensional stability while depositing a suitable amount of material on the skin during normal use. Hardness of sticks can be determined by a variety of methods, including American Society for Testing and Materials (ASTM) Method D-5. This method involves the use of a needle or polished cone of particular weight and dimension, which is allowed to travel downward through the stick material for a predetermined period of time. The distance traveled by the needle or cone is a relative measure of the stick hardness. Utilizing Method D-5, with an ASTM-D1321 arrowhead-type penetration needle (Model 13-401-10, sold by Fischer Scientific Company) weighing 50 grams, and a Model 13-399-10 Penetrometer (sold by Fischer Scientific Company) the cosmetic sticks of the present invention preferably yield an average penetration value of from about 60 to about 160 millimeters, more preferably from about 100 to about 160 millimeters, over a period of 5 seconds. These values represent an average penetration for sticks within a given production batch, since such penetration values may vary from stick to stick within the batch.

Liquid Base Material:

The cosmetic sticks of this invention contain one or more liquid materials, herein a "liquid base material", that forms the base matrix of the solid stick when combined with benzylidene sorbitol. (As used herein, "liquid" materials are those that are liquid at ambient conditions.) As will be appreciated by those skilled in the art, the selection of a particular liquid base material will vary depending upon the characteristics of the cosmetic stick desired. In particular, the liquid base materials useful in these gel sticks may be selected to provide such cosmetic benefits as emolliency or a cooling sensation when applied to the skin. Also, as will be appreciated by those skilled in the art, the specific liquid base material must be of a type, and present in an amount sufficient, to solubilize the $C_{14}$-$C_{16}$ fatty alcohol and other components to be used in the present sticks.

Liquid base materials useful herein include lower monohydric alcohols, polyhydric alcohols, and mixtures thereof. Water may also be used as a liquid base material, but is preferably present at levels of about 5% or less. Among the base materials useful herein are ethanol, isopropanol, n-propanol, n-butanol, isobutanol, tert-butyl alcohol, ethylene glycol, propylene glycol, trimethylene glycol, glycerine, 1,3-butane diol, 1,4 butane-diol, and mixtures thereof. Ethanol, propylene glycol, and mixtures thereof are among the preferred liquid base materials useful herein. Liquid base materials are disclosed in the following patent documents, all incorporated by reference herein: U.S. Pat. No. 2,900,306, Slater, issued Aug. 18, 1959; U.S. Pat. No. 3,255,082, Barton, issued June 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; and European Patent Specification No. 107,330, Luebbe, et al., published May 2, 1984. Preferred liquid base materials useful in the present gel sticks are described in U.S. Pat. No. 4,504,465, Sampson, et al., issued Mar. 12, 1985 (incorporated by reference herein). A variety of liquid base materials are also described in the following documents, all incorporated by reference herein: S. Plechner, "Antiperspirants and Deodorants", 2 *Cosmetics, Science and Technology*, 373-416 (M. Balsam and E. Sagarin ed. 1972); C. Fox, "Gel and Sticks Review and Update", 99 *Cosmetics & Toiletries* 19-52 (1984); and "Gels and Sticks Formulary", 99 *Cosmetics & Toiletries*, 77-87 (1984).

Benzylidene sorbitol:

The compositions of this invention also include a benzylidene sorbitol, which serves as a gelling agent for the liquid base material of the invention. Such materials are generally disclosed in British Patent Specification No. 1,291,819, published Oct. 4, 1972 (incorporated by reference herein).

A preferred benzylidene sorbitol for use in the present compositions is dibenzylidene monosorbitol acetal (DBMSA). This material is commercially available, such as Gell-All-D (manufactured by New Japan Chemical Co., Ltd.) and Millithix 925 (manufactured by Milliken Chemical, Division of Milliken & Company).

$C_{14}$-$C_{16}$ fatty alcohol:

The cosmetic sticks of this invention contain one or more fatty alcohols, herein a "$C_{14}$-$C_{16}$ fatty alcohol". Such fatty alcohols include myristyl alcohol (1-tetradecanol), cetyl alcohol (1-hexadecanol) and mixtures thereof. Cetyl alcohol is particularly preferred for use in the present cosmetic sticks. Although essentially pure $C_{14}$-$C_{16}$ fatty alcohols are preferred, small amounts of other fatty alcohols may also be present, such as $C_{12}$ or $C_{18}$ fatty alcohols, particularly in commercially-available materials which typically contain mixtures of fatty alcohols.

Optional "Non-active" Components:

The compositions of this invention preferably contain optional components which modify the physical characteristics of the cosmetic sticks. Such components include hardeners, strengtheners, emollients, colorants, perfumes, emulsifiers, and fillers. Optional components, useful herein, are disclosed in the following patent documents, all incorporated by reference herein: U.S. Pat. No. 3,255,082, Barton, issued June 7, 1966; U.S. Pat. No. 4,049,792, Elsnau, issued Sept. 20, 1977; U.S. Pat. No. 4,137,306, Rubino, et al., issued Jan. 30, 1979; U.S. Pat. No. 4,279,658, Hooper, et al., issued July 14, 1981; and European Patent Specification No. 117,070, May, published Aug. 29, 1984.

One preferred optional component is a volatile silicone oil, at a level of from about 1% to about 20%, preferably from about 3% to about 10%. (As used herein "volatile" refers to those materials which have a measurable vapor pressure at ambient temperature.) Such volatile silicon oils serve to reduce foaming or frothing of the liquid base materials of the present sticks in use, as well as to provide emollient characteristics. A description of various volatile silicone oils is found in Todd, et al., "Volatile Silicone Fluids for Cosmetics", 91 *Cosmetics & Toiletries* 27-32 (1976), incorporated by reference herein. Preferred silicone include the polydimethylsiloxanes having from 3 to about 9 silicon atoms. Examples of silicone oils useful herein include: Dow Corning 344, Dow Corning 345 and Dow Corning 200 (manufactured by the Dow Corning Corporation); Silicone 7207 and Silicone 7158 (manufactured by the Union Carbide Corporation); SF 1202 (manufactured by General Electric); and SWS-03314 (manufactured by SWS Silicones, Inc.).

The instant cosmetic sticks may also contain from about 0.5% to about 10% (by weight) of an inert filler material. Suitable filler materials include talc, colloidal silica (such as Cab-O-Sil, sold by Cabot Corp.), clays (such as bentonite), and mixtures thereof. The use of such fillers as stabilizing agents in cosmetic sticks is disclosed in U.S. Pat. No. 4,126,679, Davy et al., issued Nov. 21, 1978 (incorporated by reference herein).

The cosmetic sticks of the present invention may also include perfumes, emulsifiers, and coloring agents. These components are each preferably present at levels from about 0.1% to about 5.0% (by weight).

Optional "Active" Components:

Preferred embodiments of the instant cosmetic sticks contain a safe and effective amount of one or more components, herein "active components", which are meant to be deposited upon human tissue. Active components include astringents, bacteriostats, fungistats, pigments, dyes, colorants, perfumes, emollients, ultra violet absorbers, and mixtures thereof. The active components must be stable in the formulations of the instant invention. A "safe and effective" amount of an active component is that amount which yields the desired benefit at a reasonable benefit/risk ratio for human usage. Various active components among those useful in this invention are described in U.S. Pat. No. 4,226,889, Yuhas, issued Oct. 7, 1980 (incorporated by reference herein).

Particularly preferred embodiments of the present invention are useful as antiperspirants. Thus, antiperspirant sticks according to the present invention additionally comprise a safe and effective amount of an antiperspirant material, i.e., a compound or composition having antiperspirant activity. Astringent metallic salts are preferred antiperspirant compounds, and may be incorporated in the instant compositions at levels of from about 10% to about 70%, preferably from about 15% to about 50%, most preferably from about 15% to about 40%.

Preferred astringent metallic salts include the inorganic and organic salts of aluminum, zirconium and zinc, and mixtures thereof. Particularly preferred are the aluminum and zirconium salts, such as aluminum halides, aluminum hydroxyhalides, zirconyl oxyhalides, zirconyl hydroxyhalides, and mixtures thereof. Such metal salts, and complexes thereof, are described in European Patent Specification No. 117,070, May, published Aug. 29, 1984 (incorporated by reference herein) and U.S. Pat. No. 4,137,306, Rubino, et al., issued Jan. 30, 1979 (incorporated by reference herein).

Preferred aluminum salts include those of the formula

$$Al_2(OH)_aCl_b \cdot xH_2O$$

wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5, and "⅔ basic chlorhydroxide", wherein a=4. Processes for preparing aluminum salts are disclosed in the following documents, all incorporated by reference herein: U.S. Pat. No. 3,887,692, Gilman, issued June 3, 1975; U.S. Pat. No. 3,904,741, Jones, et al., issued Sept. 9, 1975; U.S. Pat. No. 4,359,456, Gosling, et al., issued Nov. 16, 1982; and British Patent Specification No. 2,048,229, Fitzgerald, et al., published Dec. 10, 1980. Mixtures of aluminum salts are described in British Patent Specification No. 1,347,950, Shin, et al., published Feb. 27, 1974 (incorporated by reference herein).

Zirconium salts are also preferred for use in antiperspirant sticks of the present invention. Such salts are of the general formula

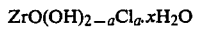
$$ZrO(OH)_{2-a}Cl_a \cdot xH_2O$$

wherein a is from about 1 to about 2, preferably from about 1.5 to about 1.87; x is from about 1 to about 7; and wherein a and n may have non-integer values. These zirconium salts are disclosed in Belgium Pat. No. 825,146, Schmitz, issued Aug. 4, 1975 (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein: U.S. Pat. No. 2,814,585, Daley, issued Nov. 26, 1957; U.S. Pat. No. 3,679,068, Leudders, et al., issued Feb. 12, 1974; U.S. Pat. No. 4,017,599, Rubino, issued Apr. 12, 1977; U.S. Pat. No. 4,120,948, Shelton, issued Oct. 17, 1978; and UK Patent Application No. 2,144,992, Callaghan, et al., published Mar. 20, 1985.

As is appreciated by thoses skilled in the art, certain of the antiperspirant materials described above may be ineffective in, or lead to instability of, the gel sticks of this invention. Accordingly, antiperspirant sticks of this invention may contain a buffering agent so as to maintain a pH of at least about 6.0 in the composition. Such buffering agents are described in U.S. Pat. No. 4,154,816, Roehl, et al., issued May 15, 1979, U.S. Pat. No. 4,346,079, Roehl, issued Aug. 24, 1982; and U.S. Pat. No. 4,518,582, Schamper, et al., issued May 21, 1985 (all incorporated by reference herein).

Among the preferred cosmetic sticks of the present invention are those which also include a safe and effective amount of deodorant materials, such as bacteriocides and fungicides, or mixtures thereof. Such deodorant materials are usually present at levels of from about 0.1% to 10% (by weight). Suitable deodorants include bacteriostatic quaternary ammonium compounds such as cetyl-trimethyl ammonium bromide, cetyl pyridinium chloride, benzethonium chloride, diisobutyl phenoxy ethoxy ethyl dimethyl benzyl ammonium chloride, sodium N-lauryl-sarcosine, sodium N-polymethyl sarcosine, lauroyl sarcosine, N-myristoyl glycine, potassium N-lauroyl sarcosine, stearyl trimethyl ammonium chloride, and mixtures thereof. Other suitable deodorant materials include 2,4,4'-trichloro-2'hydroxydiphenyl ether and sodium bicarbonate. Particularly preferred deodorant compositions utilize a diaminoalkyl amide, such as L-lysine hexadecyl amide, as disclosed in U.S. Pat. No. 3,574,747, Denning, issued Apr. 13, 1971 (incorporated by reference herein).

Methods:

The compositions of this invention are made by methods that will be appreciated by those of skill in the art. Similar methods are described in "Gels and Sticks Formulary", 99 *Cosmetics & Toiletries* 77–84 (1984), incorporated by reference herein. Such methods generally involve admixture of the benzylidene sorbitol to the liquid base materials upon heating to a temperature sufficient to dissolve the benzylidene sorbitol. Such temperature is preferably from about 70° C. to about 100° C. The cetyl alcohol and optional components are added, and the solution poured into stick forms. A solid gel then forms upon cooling. As the stick composition may solidify rapidly upon cooling, care should be taken so as to maintain an elevated temperature while mixing and processing the composition.

The following non-limiting examples illustrate the compositions, processes and uses of the present invention.

EXAMPLE I

A deodorant cosmetic stick composition, according to the present invention, was made comprising:

| Component | % (by weight) |
| --- | --- |
| ethanol | 41.33 |
| propylene glycol | 41.39 |
| cetyl alcohol | 4.99 |
| Millithix 925* | 3.02 |
| cyclomethicone (D5) | 4.98 |
| L-lysine hexadecylamide | 2.99 |

| Component | % (by weight) |
| --- | --- |
| colorants | 1.30 |

*dibenzadehyde monosorbitol acetal, manufactured by Milliken Chemical, Division of Milliken & Company The composition, comprised as above, was made by admixing the ethanol, propylene glycol, cetyl alcohol, cyclomethicone and L-lysine hexadecylamide. The solution was then heated to approximately 88° C. and the Millithix was added while stirring. After all components were in solution, the colorants were added, and the mixture heated to approximately 92%. The solution was then poured into stick forms, and solidified rapidly upon cooling.

EXAMPLE II

An antiperspirant stick composition, according to the present invention, is made comprising:

| Component | % (by weight) |
| --- | --- |
| ethanol | 38.50 |
| propylene glycol | 35.30 |
| cetyl alcohol | 3.00 |
| Millithix 925 | 3.00 |
| aluminum chlorhydrate | 20.00 |
| hexamethylene tetramine | 0.20 |

The propylene glycol, cetyl alcohol, Millithix and hexamethylene tetramine (buffering agent) are mixed thoroughly at approximately 93° C. The aluminum chlorhydrate (antiperspirant active) is dissolved in the ethanol, and the solution is then added to the propylene glycol mixture. The mixture is heated to reflux temperature and mixed. The mixture is poured into stick forms, solidifying upon cooling.

EXAMPLE III

A deodorant cosmetic stick composition, according to the present invention, is made comprising:

| Component | % (by weight) |
| --- | --- |
| ethanol | 43.25 |
| propylene glycol | 43.30 |
| cetyl alcohol | 5.00 |
| Millithix 925 | 3.00 |
| cyclomethicone | 5.00 |
| Irgasan* | 0.30 |
| fragrance | 0.15 |

*deodorant active material manufactured by Ciba-Geigy, Ltd.

A deodorant stick, comprised as above, is made in a manner similar to that described in Example I.

What is claimed:

1. In a transparent deodorant or antiperspirant stick composition comprising:
   (a) from about 10% to about 97% of a liquid base material selected from the group consisting of monohydric alcohols, polyhydric alcohols and water and mixtures thereof; and
   (b) from about 1% to about 10% of a benzylidene sorbitol;
   (c) from about 10% to about 50% of one or more astringent salts or deodorant active materials
   wherein the improvement comprises the addition of from about 1% to about 15% of a $C_{14}$–$C_{16}$ fatty alcohol.

2. A cosmetic stick composition, according to claim 1, wherein said liquid base material is selected from the group consisting of ethanol, isopropanol, n-propanol, n-butanol, isobutanol, tert-butyl alcohol, ethylene glycol, propylene glycol, trimethylene glycol, glycerine, 1,3 butane diol, 1,4 butane diol, and mixtures thereof.

3. A cosmetic stick composition, according to claim 2, wherein said liquid base material is selected from the group consisting of ethanol, propylene glycol, and mixtures thereof.

4. A cosmetic stick composition, according to claim 1, wherein said $C_{14}$–$C_{16}$ fatty alcohol is cetyl alcohol.

5. A cosmetic stick composition, according to claim 4, wherein said $C_{14}$–$C_{16}$ fatty alcohol is present at a level of from about 3% to about 7%.

6. A cosmetic stick composition, according to claim 1, wherein said benzylidene sorbitol is present at a level of from about 2.5% to about 3.5%.

7. A cosmetic stick composition, according to claim 1, additionally comprising a volatile silicone oil.

8. A cosmetic stick composition, according to claim 7, wherein said active component is an antiperspirant material.

9. A cosmetic stick composition, according to claim 7, wherein said active component is a deodorant material.

* * * * *